United States Patent [19]

Shannon

[11] 4,135,509
[45] Jan. 23, 1979

[54] FLUID PRESSURE MANOMETER

[75] Inventor: Thomas J. Shannon, St. Joseph, Mo.

[73] Assignee: Sherwood Medical Industries Inc., St. Louis, Mo.

[21] Appl. No.: 791,105

[22] Filed: Apr. 26, 1977

[51] Int. Cl.² ............................................. A61B 5/02
[52] U.S. Cl. ........................... 128/2.05 D; 128/214 E; 128/DIG. 13; 206/364; 206/459
[58] Field of Search ..................... 128/2.05 D, 2.05 N, 128/213, 214 A, 214 B, 214 C, 214 D, 214 E, 214 F, 214 R, DIG. 12, DIG. 13; 206/569-571, 305, 363-364, 438-439, 557, 562, 564, 459; 73/388 R, 401, 402

[56] References Cited

U.S. PATENT DOCUMENTS

| | | | |
|---|---|---|---|
| 2,202,163 | 5/1940 | Mulford et al. | 128/214 R |
| 2,625,153 | 1/1953 | Baum | 128/2.05 D |
| 3,013,656 | 12/1961 | Murphy, Jr. | 206/571 |
| 3,062,202 | 11/1962 | Hyman et al. | 128/2.05 D |
| 3,435,819 | 4/1969 | Reynolds et al. | 128/2.05 D |
| 3,473,387 | 10/1969 | Meriam | 73/401 |
| 3,690,676 | 10/1954 | Heuboski et al. | 73/402 |
| 3,730,168 | 5/1973 | McWhorter | 128/2.05 D |
| 3,897,786 | 8/1975 | Garnett et al. | 206/439 |
| 3,951,145 | 4/1976 | Smith | 128/214 R |

OTHER PUBLICATIONS

"Direct Determination of Venous Pressure", Surg. Equip., vol. 2, #3, May–Jun. 1935.

Primary Examiner—Robert W. Michell
Assistant Examiner—Francis J. Jaworski
Attorney, Agent, or Firm—Stanley N. Garber; William R. O'Meara

[57] ABSTRACT

A disposable venous blood pressure manometer of provided which includes a transparent tray having a longitudinal interior channel with a transparent plastic manometer tube disposed in the channel, a calibrated scale member in the tray behind the tube, and a cover closing the back of the tray and which may be used as a label. The cover and body member provide a container which may contain a plastic extension tube and a three-way valve. The container can be opened by peeling back a bottom end portion of the cover from the body member. The extension tube and valve can then be removed for use in connecting the manometer tube in an infusion and pressure measuring system. The level of liquid in the manometer tube during use and the scale can be seen through the transparent tray for taking pressure readings. The container performs a functional part of the manometer during use.

22 Claims, 6 Drawing Figures

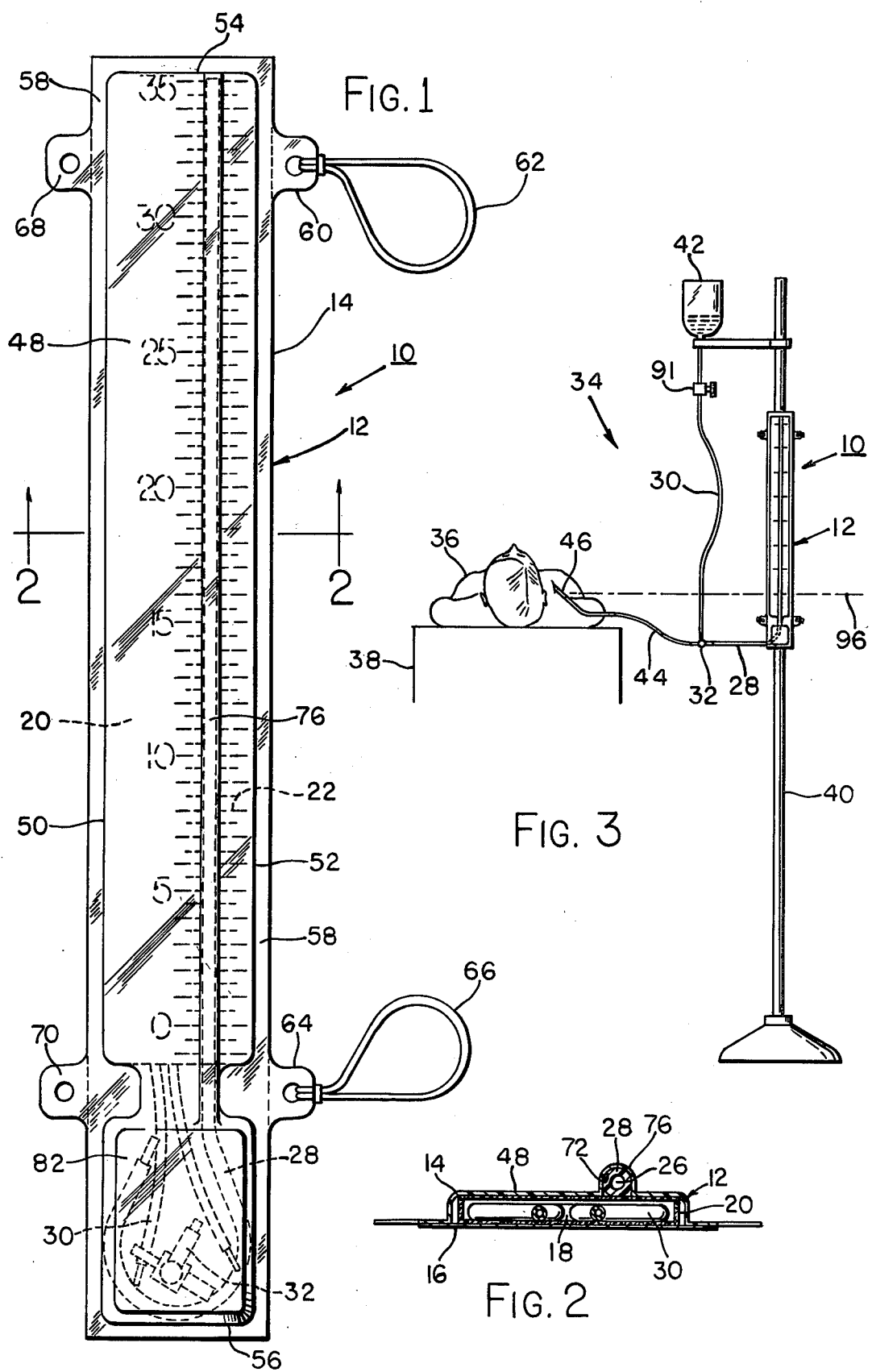

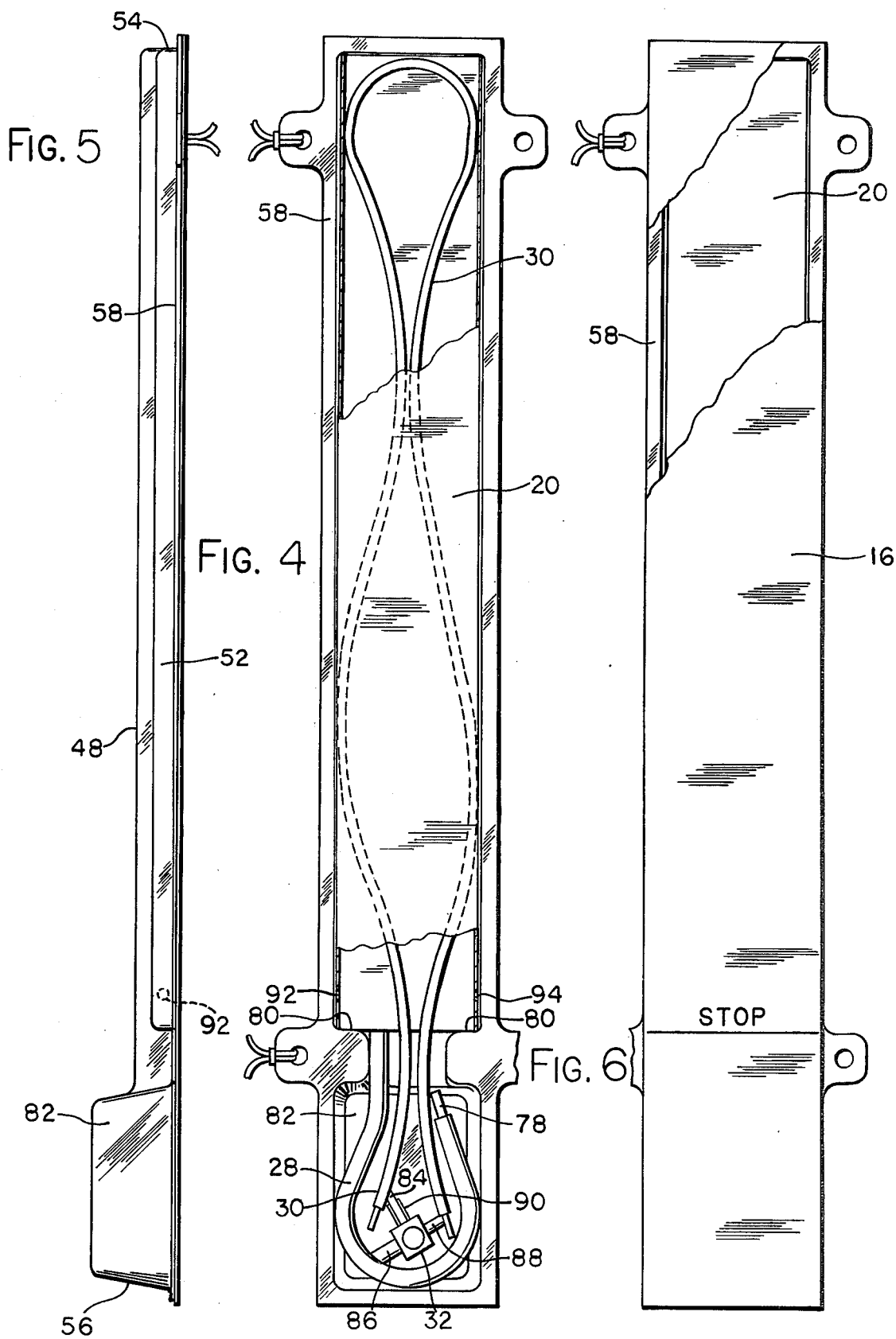

FLUID PRESSURE MANOMETER

BACKGROUND OF THE INVENTION

This invention relates to manometers and more particularly to a liquid manometer for measuring body fluid pressure.

Body fluid pressure indicating devices, such as direct venous pressure manometers, generally include a manometer tube with a scale which is connected to an intravenous catheter disposed in a vein of the patient. The level of liquid in the tube indicates the pressure of the blood in the vein. Central venous pressure (CVP) is often monitored during post-surgery therapy and is generally accompanied by intravenous administration of a liquid such as a saline solution. Central venous pressure may be monitored, for example, by measuring blood pressure in the superior vena cava or subclavian vein.

Such manometers are generally packaged in individual containers which may be in the form of wrappers or boxes. The packaged manometer may contain an extension tube and a three-way stopcock or valve for connecting the manometer in a blood pressure measuring and liquid infusion system. Also, in some cases, an attached sighting device is included for the purpose of accurately adjusting the position of the manometer is relative to the patient so that the zero reading on the manometer scale is at the same level as the right atrium of the heart of the patient in order to obtain correct readings. U.S. Pat. No. 3,934,576 illustrates the use of a three-way stopcock and of a sighting device connected to a manometer.

Such packaged manometers have certain disadvantages. For example, when the manometer is to be used, the container or packaging material must be removed from the manometer and then discarded such as by placing it into a waste receptacle. The packing container, in some cases, represents a significant portion of the total cost of the manometer. Also, the sight means may add significantly to the cost of the device.

SUMMARY OF THE INVENTION

It is therefore an object of the present invention to provide a liquid manometer that does not require a separate, individual packaging container that must be removed from the manometer when it is to be functionally used.

Another object is to provide a packaged blood pressure manometer wherein the packaging container serves a functional purpose when the manometer is in functional use.

Still another object is to provide an economical, packaged venous pressure manometer wherein the packaging maintains parts sterile before being opened and is a functional part of the manometer when the manometer is utilized to measure blood pressure, and wherein the packaged manometer is quickly and easily opened and connected in a pressure measuring system.

Still another object is to provide a central venous pressure manometer of the above type which has simple and economical sight means for adjusting the position of the manometer relative to the patient for obtaining proper pressure readings.

In accordance with one form of the present invention, a liquid manometer is provided which includes an elongate body member, a cover connected to the body member to define an enclosed chamber, a lumen extending longitudinally within the chamber, and with the body member being transparent at least adjacent the lumen so that liquid in the lumen is visible through the body member for measuring pressure.

These and other objects and advantages of the present invention will be apparent from the following detailed description and accompanying drawing.

BRIEF DESCRIPTION OF THE DRAWING

FIG. 1 is an elevational view of a liquid manometer in accordance with a preferred embodiment of the invention;

FIG. 2 is a cross-sectional view taken along line 2—2 of FIG. 1;

FIG. 3 is an elevational view of a pressure measuring system utilizing the manometer of FIG. 1;

FIG. 4 is a back elevational view of the manometer of FIG. 1 with the back cover removed;

FIG. 5 is a side elevational view of the manometer of FIG. 1; and

FIG. 6 is a back elevational view of the manometer of FIG. 1 with a portion of the back cover broken away.

DESCRIPTION OF THE PREFERRED EMBODIMENT

Referring now to the drawings, and particularly to FIGS. 1 and 2, a packaged liquid manometer 10 in accordance with the present invention is shown including a container 12 having an elongate container body member 14 and a container cover or lid 16 closing the container and defining with the body member 14 a closed chamber 18. Disposed within chamber 18 is a scale member 20 having indicia extending longitudinally of the container and providing a scale 22, for example, graduated in centimeters. Also disposed in chamber 18 is a fluid passageway or lumen 26 extending along the calibrated scale 22 and shown as the lumen of a transparent plastic manometer tube 28. Also, a plastic extension tube 30 and a suitable conventional valve, such as a three-way stopcock or valve 32, are disposed in chamber 18, the purpose and function of which will be described hereinafter.

In FIG. 3, an intravenous administration and venous blood pressure measuring system, indicated generally at 34, and which will subsequently be described in greater detail, is shown utilizing the manometer 10 after it has been opened and its parts connected for measuring the central venous blood pressure of a patient 36 shown in a supine position on a table or bed 38. The liquid manometer 10 is shown secured to a vertical stand 40 with the three-way valve 32 connected to the manometer tube 28, an intravenous or infusion bottle 42 by means of the extension tube 30, and to a tube 44 connected to an intravenous catheter 46 that has been inserted in the vein of the patient. The catheter 46 may be placed in the superior vena cava or vena subclavia for measuring central venous pressure. Briefly, when a pressure reading is taken, the valve 32 may be manually operated to interrupt the infusion of liquid to the patient and place the liquid in manometer tube 28 in communication with the catheter 44. All of the parts of the packaged manometer 10 of FIG. 1, including the package or container 12, are functionally employed in the system 34 of FIG. 3.

Referring now again to FIGS. 1 and 2, and also to FIGS. 4-6, the body member 14 is in the shape of a tray formed of a suitable transparent plastic, for example, it may be a thermo-formed tray of polyvinyl chloride. The body member or tray 14 has a bottom wall 48 which serves as the front side of the manometer, a pair of parallel longitudinally extending opposed side walls 50 and 52, and a pair of opposed end walls 54 and 56. The side and end walls are integral with and extend generally normal to the plane of the major portion of the bottom wall 48. An outwardly extending flange 58 is integrally connected to the opposed side and end walls and extends around the entire periphery of the body member 14. An outwardly extending integral tab 60 near the top of the body member is provided with a rubberband 62 which may be looped or knotted through an opening in the tab. Similarly, near the bottom of the body member 14 there is provided another integral tab 64 with an opening and a rubberband 66 connected to the tab. The bands 62 and 66 are adapted to extend around the stand 40 (FIG. 3) and be respectively looped over the integral tabs 68 and 70 on the body member so as to securely hold the manometer on the stand 40 while in use.

The body member 14 is preformed with an integral channel 72 in the bottom wall 48 which is open to chamber 18. The channel 72 extends longitudinally of the body member and receives the plastic manometer tube 28 which may be held in place by a friction fit or by a suitable cement. Channel 72 is shown formed by a wall 76 which is raised out of the plane of the main portion of body member 14. The upper end of tube 28 is open and slightly spaced from the inner surface of end wall 54 within chamber 18 and may be provided with an antibacterial filter (not shown) at its upper end. The lower end of tube 28 is open and is also disposed within the chamber 18 in the closed or packaged condition of the manometer 10. The lower end portion of tube 28 extends from the lower end of channel 72 and is provided with a Luer or tapered connector 78 (FIG. 4). The scale member 20 is disposed in chamber 18 between the bottom wall 48 of the body member 14 of the inside wall of cover 16. The scale member 20 is formed, for example, of a suitable paperboard in the form of a tube which is rectangular in cross-section and has indicia printed on one side forming the scale 22.

The scale member 20 is longitudinally disposed within chamber 18 between the inner side of the upper end wall 54 and internal walls 80 formed by a narrowed chamber portion (FIGS. 1 and 4) near the bottom. Scale 22 is disposed adjacent the tube 28 and can be easily read through the transparent body member 14.

As seen in FIGS. 1, 4 and 5, the lower end portion of the body member 14 is provided with an enlarged portion 82 so that chamber 18 has a greater volume at the lower end and can therefore readily accomodate end portions of tubes 28 and 30, and the valve 32.

The cover 16 may be formed of a suitable antibacterial paper or plastic which is attached to the back side of flange 58 to completely sealingly close the chamber 18. The cover is preferably pervious to sterilizing gas so that the parts within the packaged manometer 10 can be sterilized after the container 12 is closed.

The cover 16 is of a material which is suitable for bonding, such as heat bonding, to flange 58 and which will permit a portion of the cover to be manually peeled back from a portion of the body member when the packaged manometer is opened for use. For example, cover 16 may be "Tyvek", a product of DuPont, and which is a spun bonded polyethylene having a coating which provides a peelable heat bonded seal with flange 18. As shown in FIG. 6, a stop line and word "stop" are printed on the back side of cover 16 to indicate that the cover can be conveniently peeled back up to the stop line and the tube 30 and valve 32 removed without removing or detaching the entire cover from the body member 14. The cover 16 may serve also as a label and having other printing on it (not shown).

The three-way stopcock or valve 32 is provided with three ports 84, 86 and 88, and a control handle 90. Generally, with stopcocks of this type, fluid can flow between any two ports, as determined by the position of the handle, while the third port is closed. The ports may have Luer tapered surfaces for readily connecting the three ports to the tubes 28, 30 and 44 as seen in FIG. 3. Also, a conventional, adjustable pinch valve 91 or the like may be connected to the tube 20 to vary the rate of infusion liquid to the patient.

In order to adjust the position of manometer 10 so as to accurately position the zero point of the scale 22 at the same height as the patient's heart or right atrium, the manometer is provided with a simple and inexpensive sight shown as including a pair of sighting holes 92 and 94 in FIG. 4. The holes 92 and 94 are formed in the opposed side walls of the scale member 20 adjacent the zero scale reading. Since the body member or tray 14 is formed of transparent plastic, the person adjusting the manometer can look through member 14 and the two aligned holes 92 and 94, and move the manometer on stand 40 until the desired area of the patient is seen through the holes. In FIG. 3, the line 96 represents the desired line of sight.

When it is desired to employ the packaged manometer 10 (FIG. 1), it is opened and the extension tube 30 and valve 32 removed from the container 12 and connected between the infusion bottle 42 (FIG. 3) and tube 44. With the catheter 44 properly placed in the patient's vein, such as in the subclavian vein, the valve handle 90 may be positioned to allow infusion liquid to flow into the patient while isolating or closing off the manometer tube 28 from tubes 30 and 44. Care, of course, must be taken to avoid the introduction of air into the patient's vein.

After the container 12 of the manometer 10 has been accurately positioned relative to the patient 36, such as by use of the sight holes 92 and 94 as previously described, the valve handle 90 is adjusted to connect the manometer tube 28 in fluid communication with the tube 30 while the tube 44 is isolated or shut off from tubes 28 and 30. The liquid from bottle 42, which may be, for example, a saline solution, is allowed to flow into the manometer tube 28 until the liquid level rises to a point near the top of the scale, for example, to a reading of about 30 centimeters of water. Then the valve handle 90 is adjusted to connect manometer tube 28 in fluid communication with tube 44 while isolating the tube 20 from both tubes 28 and 44. The liquid level in tube 28, as will be seen through the body member 14, will drop in tube 28 to the value representative of the central venous pressure of the patient. After obtaining a pressure reading in centimeters of water, the valve 32 may then be adjusted again to connect the catheter 46 in communication with the infusion bottle 42 to again infuse the saline solution.

All of the parts of the packaged manometer 10 of FIG. 1 are actually used in the system 34, and no additional packaging materials are required for the individual manometer 10. No packaging materials are separated and discarded when employing the manometer 10 in a pressure measuring system. The packaging container 12 not only serves to maintain the manometer parts inside the container sterile in the packaged condition of the manometer (FIG. 1), but is a functional part of the manometer, it serving to support the scale member 20 and manometer tube 28 when the manometer is functioning in a pressure measuring system (FIG. 3). Also, the sight means which includes portions of the scale member and holes 92 and 94, provides a simple, effective and economical means for properly positioning the manometer relative to the patient.

As various changes could be made in the above construction without departing from the scope of the invention, it is intended that all matter contained in the above description and shown in the accompanying drawings be interpreted as illustrative and not in a limiting sense.

What is claimed is:

1. A packaged liquid manometer for measuring fluid pressure wherein the manometer package constitutes an integral structural portion of the manometer, comprising an elongate body member defining a first package portion, cover means connected to said body member to define a closed chamber therebetween, said cover means defining a second package portion, means defining a manometer lumen extending longitudinally within said chamber and having opposed upper and lower ends within said chamber, said upper end being open to said chamber for the flow of air between the chamber and the upper portion of said lumen, said body member being transparent in at least portions thereof adjacent said lumen so that when liquid is in said lumen its level can be seen through said body member, and scale means including indicia extending longitudinally adjacent said lumen for indicating pressure, at least a portion of said cover means being separable from a portion of said body member to permit access to said lower end of said lumen for connecting said lumen with a source of liquid and connecting said chamber with the atmosphere, whereby said lower end of said lumen is contained within said chamber and is inaccessible prior to use but accessible for connection to said source of liquid after said portion of said cover means is separated from said portion of said body member.

2. The liquid manometer of claim 1 wherein said means defining a lumen comprises a transparent plastic tube carried by body member.

3. The liquid manometer of claim 2 wherein said body member has a channel formed therein which extends longitudinally of said body member and is open to said chamber, said plastic tube being disposed in said channel.

4. The liquid manometer of claim 2 wherein said body member is a plastic tray and said cover means is formed of sheet material.

5. The liquid manometer of claim 1 wherein said body member is comprised of transparent plastic material.

6. The liquid manometer of claim 1 further including fluid valve means within said chamber adapted to be removed from said chamber and connected in fluid communication with said lumen and a source of liquid.

7. The liquid manometer of claim 6 further including an auxillary tube in said chamber for subsequent removal therefrom for connection in a fluid system, and said means defining a lumen comprises a transparent plastic tube.

8. The liquid manometer of claim 1 wherein said body member is generally tray-shaped and includes a bottom wall and a pair of opposed, generally parallel, side walls extending generally normal to the plane of said bottom wall.

9. The liquid manometer of claim 1 wherein said body member includes a bottom wall a pair of opposed end walls and a pair of opposed side walls integrally connected together and to said bottom wall and all extending generally normal to said bottom wall, and means connecting said cover means to said end and side walls.

10. The liquid manometer of claim 9 wherein said cover means is pervious to sterilizing gas to permit sterilization of the interior surfaces of the manometer.

11. The liquid manometer of claim 8 wherein said cover means comprises a sheet material connected to said body member and having a portion thereof peelable from a portion of said body member.

12. The liquid manometer of claim 11 wherein said scale means includes an element within said chamber having an elongate wall with said indicia on said elongate wall and visible through said body member.

13. The liquid manometer of claim 1 wherein said body member and said cover define a container which is pervious to a sterilization gas.

14. The liquid manometer of claim 1 wherein said body member is in the form of a tray having a bottom wall, a pair of opposed transversely extending end walls, a pair of opposed longitudinally extending side walls, said end and side walls being integrally connected with said bottom wall and extending generally normal to the plane of the major portion of said bottom wall, and flange means integrally connected to said end and side walls and extending in a plane substantially parallel with said plane of said major portion of said bottom wall, said cover means being sealingly connected to said flange means.

15. The liquid manometer of claim 14 wherein a portion of said cover means is peelable from said flange means.

16. The liquid manometer of claim 15 wherein said body member is of transparent thermoplastic material.

17. The liquid manometer of claim 1 wherein said lower end of said lumen means is removable from said chamber after said portion of said cover means is separated from said portion of said body member for connection with a source of liquid.

18. A packaged liquid manometer for measuring fluid pressure comprising an elongate body member, cover means connected to said body member to define a closed chamber therebetween, means defining a lumen extending longitudinally within said chamber and having opposed ends within said chamber, said body member being transparent in at least portions thereof adjacent said lumen so that when liquid is in said lumen its level can be seen through said body member, said body member including a bottom wall, a pair of opposed end walls and a pair of opposed side walls integrally connected together and to said bottom wall with all of said end and side walls extending generally normal to said bottom wall, and scale means in said chamber including a hollow elongate four sided element generally rectangular in cross section and having indicia on one of said sides extending longitudinally adjacent said lumen, said indicia being visible through said body member, said cover means including sheet of material, said sheet material being connected to said end and side walls of said body member, said sheet of material having at least a portion thereof peelable from a portion of said body member to permit access to one of said lumen ends for connecting said lumen with a source of liquid.

19. The liquid manometer of claim 18 further including an auxillary plastic tube extending into said hollow elongate four-sided element.

20. The liquid manometer of claim 13 wherein said body member is formed with an enlargement at one end thereof, said valve being disposed in said enlargement.

21. The liquid manometer of claim 18 wherein said indicia includes a zero pressure indicia, said four-sided element has a pair of spaced, aligned sight openings therein adjacent to said zero pressure indicia for positioning the manometer by sight relative to a source of fluid pressure.

22. A packaged liquid manometer for measuring fluid pressure comprising an elongate body member, cover means connected to said body member to define a container pervious to a sterilization gas and having a closed chamber between said cover means and said body member, means defining a lumen extending longitudinally within said chamber and having opposed ends within said chamber, said body member being transparent in at least portions thereof adjacent said lumen so that when liquid is in said lumen its level can be seen through said body member, scale means including indicia extending longitudinally adjacent said lumen, at least a portion of said cover means being separable from a portion of said body member to permit access to one of said lumen ends for connecting said lumen with a source of liquid, and sight means for relatively accurately positioning the manometer relative to a patient's heart when the manometer is functionally used to measure the patient's blood pressure including openings in said scale means, said body member being transparent in areas adjacent said openings so that sightings can be made through said openings and said body member.

* * * * *